US007820691B2

(12) United States Patent
Shcherbakova et al.

(10) Patent No.: US 7,820,691 B2
(45) Date of Patent: Oct. 26, 2010

(54) INDOLOQUINOLINE COMPOUNDS AS CALCIUM CHANNEL BLOCKERS

(75) Inventors: Irina Shcherbakova, Midvale, UT (US); Yuri Nikolyukin, Moorsetown, NJ (US)

(73) Assignee: MediProPharma, Inc., Midvale, UT (US)

( * ) Notice: Subject to any disclaimer, the term of this patent is extended or adjusted under 35 U.S.C. 154(b) by 0 days.

(21) Appl. No.: 11/890,166

(22) Filed: Aug. 3, 2007

(65) Prior Publication Data
US 2008/0051426 A1    Feb. 28, 2008

Related U.S. Application Data

(60) Provisional application No. 60/840,596, filed on Aug. 28, 2006.

(51) Int. Cl.
*A61K 31/4745* (2006.01)
*C07D 471/02* (2006.01)
(52) U.S. Cl. ............................ 514/285; 546/70; 546/15; 514/278
(58) Field of Classification Search ................ 514/285, 514/278; 546/70, 15
See application file for complete search history.

(56) References Cited

FOREIGN PATENT DOCUMENTS

| SU | 2 064 793 | 8/1980 |
| SU | 2064793 C1 | 8/1980 |
| UA | 24393 A | 7/1998 |
| WO | WO 2008/106659 | 9/2008 |
| WO | WO 2008/109343 | 9/2008 |

OTHER PUBLICATIONS

Dulenko, V.I. et al.: Synthesis of condensation products of indolo[2,3-c]pyrylium salts and beta-carbolines. Khimiya Geterot. Soed. vol. 3, pp. 363-366, 1985 ( see english translation pp. 302-305 ).*
Kibalny, A.V. et al.: Tetracyclic beta-carbolines. The neuroprotector carbacetam, its derivatives and independent synthesis. Fiziologichno Aktivni Rechovini, vol. 2, pp. 23-29, 2002.*
Compounds with RN 118776-13-9 and RN 123199-88-2 ( disclosed in 1989 ).*
Lader et al., "Withdrawing Benzodiazepines In Primary Care," CNS Drugs, vol. 23, 2009, pp. 19-34.
A. V. Kibal'nyi et al., "Tetracyclic β-Carbolines. The Neuroprotector Carbacetam, Its Derivatives And Countercurrent Synthesis," Fisiolohichno aktyvni rechovyny, No. 2 (34), 2002, pp. 23-29.
Komissarov, et al., Noncoincidence of the Anxiolytic, Sedative, and Antispasmodic Properties in Harman Derivatives, Khimiko-Farmatsevticheskii Zhurnal, Mar. 1986, vol. 19, No. 3, pp. 187-191.
Komissarov, et al., Synthesis and Pharmacological Properties of 1-Alkyl-3,4-Tetramethylene-β-Carbolines, Khimiko-Farmatsevticheskii Zhurnal, Jun. 1990, vol. 23, No. 6, pp. 471-474.

Dulenko, et al., Synthesis of Condensed Derivatives of Indolo[2-3-c]pyrylium Salts and β-Carbolines, Khimlya Geterotsikicheskikh Soedinenii, Mar. 1985, No. 3, pp. 363-366.
Tolkunov, et al., Condensed Pyridine Bases. Khimiya Geterotsiklicheskikh Soedinenii, Aug. 1995, No. 8, pp. 980-984.
International Search Report dated Jul. 25, 2008 that issued in International Application No. PCT/US07/17943.
Kibal'nyi et al., Fiziiologichno aktivni rechovini, "Tetracyclic B-Carbolines, Neuroprotector Carbactetam, its Derivatives and Independent Synthesis," No. 2 (34), pp. 23-29 (2002) (English Translation).
Tighineanu, et al., Tetrahedron, "Double Cycllsation of Phenylglycine-o-Carboxylic Acids," No. 36, pp. 1385-1397, (1980).
Kollmar et al., Organic Syntheses, "2-Amino-3-Fluorobenzoic Acid," vol. 10, p. 23 (2004); vol. 79, p. 196 (2002).
Holt et al., Proceedings of the Royal Society B, "Studies in Enzyme Cytochemistry II. Synthesis of Indigogenic Substrates for Esterases," vol. 148, pp. 481-494, (Apr. 8, 1958).
Holt et al., Journal of the Chemical Society, "Vibration Frequency Correlations in Heterocyclic Molecules. Part IV. Indoxyl Derivatives," pp. 1217-1223 (1958).
Stockmann et al., Tetrahedron, "Preparation of New Pyrido[3,4-b]thienopyrroles and pyrido[4,3-e]-thienopyridazines," No. 64, pp. 7626-7632 (2008).
Lukic-Panin et al., Prevention of Neuronal Damage by Calcium Channel Blockers with Antioxidative Effects after Transient Focal Ischemia in Rats, *Brain Research*, (Aug. 2, 2007), vol. 1176, pp. 143-150.
Zhang et al., N-methyl-D-asparate Receptor and L-type Voltage-Gated $Ca^{2+}$ Channel Antagonists Suppress the Release of Cytochrome C and the Expression of Procaspase-3 in Rat Hippocampus after Global Ischemia, *Neuroscience Letters*, (May 13, 2002), vol. 328, pp. 265-268.
Bağirici et al., M. Ö., Anticonvulsant Effects of Nimodipine on Penicillin-Induced Epileptoform Activity, *Acta Neurobiologiae Experimentalis*, (Jun. 1, 2006), vol. 66, pp. 123-128.
Yagami et al., Protective Effects of a Selective L-Type Voltage-Sensitive Calcium Channel Blocker, S-312-d, on Neuronal Cell Death, *Biochemical Pharmacology*, (Nov. 3, 2003), vol. 67, pp. 1153-1165.
Rose et al., Efficacy of MEM 1003, A Novel Calcium Channel Blocker, in Delay and Trace Eyeblink Conditioning in Older Rabbits, *Neurobioogy of Aging*, (Apr. 18, 2006), vol. 28, pp. 766-773.
Shutov et al., The Effect of Nimodipine on Calcium Homeostasis and Pain Sensitivity in Diabetic Rats, *Cellular and Molecular Neurobiology* (Jul. 12, 2006), vol. 26, pp. 1541-1557.

(Continued)

*Primary Examiner*—Charanjit S Aulakh
(74) *Attorney, Agent, or Firm*—Stoel Rives LLP

(57) ABSTRACT

Various calcium channel blockers and pharmaceutical compositions containing these compounds are disclosed. Calcium channel blockers are compounds capable of inhibiting calcium ion channels. Methods for preparing calcium channel blockers and their use as calcium channel antagonists are also disclosed.

25 Claims, No Drawings

OTHER PUBLICATIONS

Mamczarz et al., The $Ca^{+2}$ Channel Blockade Changes the Behavioral and Biochemical Effects of Immobilization Stress, *Neuropsychopharmacology*, (Jul. 21, 1998), vol. 20, pp. 248-254.

Handbook of Pharmaceutical Salts, Wiley-VCH (Stahl et al. eds., 2002).

J. Striessnig et al., 'Role of Voltage-Gated L-Type CA2+ Channel Isoforms for Brain Function', Biochemical Society 2006, Ion Channels: Communication Across Membranes.

* cited by examiner

INDOLOQUINOLINE COMPOUNDS AS CALCIUM CHANNEL BLOCKERS

CROSS-REFERENCE TO RELATED APPLICATIONS

This application claims the benefit of provisional patent application Ser. No. 60/840,596 filed 2006 Aug. 28 by the present inventor.

TECHNICAL FIELD

The present disclosure relates to substituted 2,3,4,7-tetrahydroindolo[2,3-c]quinoline compounds able to block calcium ion channels, and to methods for preparing and the uses of such compounds. The compounds described herein are administered to patients to achieve a therapeutic effect.

BACKGROUND

The present disclosure relates to novel 2,3,4,7-tetrahydroindolo[2,3-c]quinoline compounds, methods for preparing these compounds, pharmaceutical compositions containing these compounds and their uses as calcium ($Ca^{2+}$) channel blockers, or calcium ($Ca^{2+}$) channel antagonists.

The present disclosure relates to novel indoloquinoline compounds which have a beta-carboline central motif. It is well known from the literature that a number of beta-carboline compounds have a high affinity at the benzodiazepine (BDZ) binding sites of the gamma-aminobutyric acid (GABA) receptors, namely, $GABA_A$ complex acting as positive allosteric modulators, i.e. increasing GABA-ergic activity (see, for example, WO 92/21679; WO 93/06100). Certain beta-carboline compounds are inhibitors of the GABA-uptake by the GABA transporter protein GAT-3/4 [see GB 2,355,659 A (2001)]. Other certain beta-carboline compounds are HIV inhibitors [see WO 2004/067531 A1; US 2005/0165040 A1; U.S. Pat. No. 7,001,912 B2 (2006)], IκB-kinase complex (IKK) inhibitors (see WO 01/68648 A1; WO 2004/092167; US 2005/0239781 A1), antagonists of the intestinal hormone glucagons-like peptide 1 (GLP-1) (see WO 00/33839), inhibitors of interleukin-2 (IL-2) production (see WO 98/06719) or are able to elicit periodic amplified calcium ($Ca^{2+}$) release in beta-cells (see WO 03/065036). Prior to this disclosure, however, there was no recognition or appreciation of the efficacy of beta-carboline analogs as calcium channel blockers.

The compounds of this disclosure are particularly useful for treating diseases and conditions of mammals that are mediated by voltage-gated calcium ($Ca^{2+}$) channels. Voltage-gated calcium channels are present in neurons, and in cardiac, smooth and skeletal muscle and other excitable cells. These channels mediate the influx of $Ca^{2+}$ into cells in response to changes in membrane potential. Because of their central role in ion homeostasis and in cell signaling events, these channels are involved in membrane excitability, muscle contraction and cellular secretion, such as exocytotic synaptic transmission. Calcium channels are generally classified according to their electrophysiological properties as low-voltage activated (LVA) and high-voltage activated (HVA) channels. HVA channels are currently known to comprise at least three groups of channels, known as L-, N- and P/Q-type channels. These channels are distinguished one from another electrophysiologically as well as biochemically on the basis of their pharmacology and ligand binding properties. HVA calcium channels are formed by the heteromeric association of membrane proteins comprising at least three subunits, α ($α_1$, $α_2$), δ and β (also, γ in skeletal muscle) [see T. P. Snatch, et al., Proc. Natl. Acad. Sci. 87: 3391-3395 (1990); R. W. Tsien, et al., Trends Neurosci. 12: 349-354 (1991); M. E. Williams, et al., Neuron 8: 71-84 (1992); Y. Fujita, et al., Neuron 10: 585 (1993)]. The $α_1$ subunit alone is sufficient to form a functional channel, although the functional properties of the channel are subject to modification, particularly by the β subunit. The calcium channels exist in resting (closed), activated (open) or inactivated (desensitized) states. The resting channels open in response to depolarization of the membrane, and then transition to an inactivated state. Repolarization is required for return to the resting state.

Calcium channels are recognized as important targets for drug therapy. Calcium channel blockers are potent vasodilators and are implicated in a variety of pathological conditions, including essential hypertension, congestive heart failure, angina, arrhythmias, migraine and pain.

The calcium channel blockers approved for clinical use in the U.S.A. belong to a few different chemical classes: dihydropyridines (e.g., amlodipine, felodipine, nifedipine, nicardine, isradipine, nimodipine), benzothiazepines (e.g, diltiazem), phenylalkylamines (e.g., verapamil), and diarylaminopropylamine ether (e.g., bepridil).

The dihydropyridines, benzothiazepines and phenylalkylamines bind to distinct, but functionally coupled sites on the $α_1$ subunit of L-type calcium channels; binding of any one class of the drugs can allosterically modulate the binding of drugs in the other two classes and the high affinity $Ca^{2+}$ binding site in the channel [see G. H. Hockerman, et al., Ann. Rev. Pharmacol. Toxicol. 37: 361-396 (1997)].

These types of pharmacophores appear to have a considerable selectivity for the L-type channel in the cardiovascular system thus accounting for their general inactivity in neuronal and secretory tissues [see D. J. Triggle, Biochem. Pharmacol. 74: 1-9 (2007)]. For example, the effect of nimodipine in the clinical studies for a subgroup of brain injury patients with subarachoid hemorrhage showed a beneficial effect, though the increase in adverse reactions suffered by the intervention group may mean that the drug is harmful for some patients [see J. Langham, et al., The Cochrane Database of Systematic Reviews, 4: 1-17 (2003)].

The compounds which block calcium channels and have reduced potency for cardiovascular effects may be useful in the treatment of neurological disorders such as traumatic brain injury, traumatic shock (hemorrhage with tissue injury), stroke, acute and chronic pain, migraine, Alzheimer's disease, epilepsy, multiple sclerosis, Parkinson's disease, amyotropic lateral sclerosis, and depression [see, for example, J. Hatton, CNS Drugs 15: 553-581 (2001); J. Fritze, et al., J. Neural Tramsm Suppl. 46: 539-543 (1995); T. Yagami, et al., Biochem. Pharmacol. 67: 1153-1165 (2004); S. Moosmang, et al., J. Neurosci. 25: 9883-9892 (2005); I. Nomura, et al., Neurosci. Lett. 391: 1-6 (2005); D. Lowe, et al., ICAD 2006, abstract P4-437, Madrid).

The use of calcium channel blockers is known to be beneficial against ischemia or traumatic brain injury. Ischemic insults to the brain in stroke or traumatic brain injury produce excessive release of glutamate from depolarized nerve terminals. This excessive glutamate release in turn stimulates massive calcium entry into nerve cells, activating the biochemical cascade that results in cell death. A major pathway of calcium entry into depolarized nerve cells is through voltage-gated calcium channels. This calcium entry can be blocked by calcium channel blockers. The data demonstrated that on fluid percussion injury in rats, treatment with a calcium channel blocker, verapamil resulted in a significant improvement in posttraumatic hemodynamic depression and a restoration of the vasoreactivity [see T. Maeda, et al., *J. Neurotrauma* 22: 763-771 (2005)]. The use of calcium channel blockers has been suggested for prevention or treatment of cerebral vasospasm after acute traumatic brain injury. The suggested use is based on the hypothesis that these drugs can counteract the influx of extracellular calcium in the vascular smooth-muscle cells and prevent the blood vessel constriction [see D. I. Graham, et al., *J Neurology Neurosurgery Psychiatry* 52: 346-350 (1989)].

Recently, other calcium channel antagonists such as DP b99, CNS 1145, LOE 908, MN 153 and MEM 1003 have been shown to be neuroprotective in animal models and are presently in clinical trials [see J. Hatton, *CNS Drugs* 15: 553-581 (2001)].

There are considerable shortcomings in current usage of the approved drugs. Some calcium channel blockers cause reflex tachycardia, excessive vasodilation and gastrointestinal problems. The most common adverse side effects include headache, hypotension, nausea, flushing, dizziness, fatigue, edema, abdominal pain and constipation. With a few exceptions, the currently used drugs have a short duration of action and must be administered frequently for sustained affects.

Thus, a need exists for novel compounds as calcium channel blockers with greater tissue selectivity, increased efficacy, reduced side effects and a more favorable duration of action.

SUMMARY

The present disclosure is related to the discovery that the indoloquinoline compounds represented by Structure (I) act as blockers of calcium ($Ca^{2+}$) channels.

Also, an aspect of the present disclosure is related to the discovery that the indoloquinoline compounds of Structure (I) exhibit selectivity for blockade of the $\alpha_1$ subunit of L-type calcium channels.

Another aspect of the present disclosure is related to the discovery that the indoloquinoline compounds of Structure (I) exhibit a high degree of potency and selectivity for the dihydropyridine and benzothiazepine binding sites of the $\square_1$ subunit of neuronal L-type calcium channels.

Yet another aspect of the present disclosure is related to the discovery that the indoloquinoline compounds of Structure (I) act as inhibitors of the gamma-aminobutyric acid (GABA) chloride ($Cl^-$) channels at the tert-butylbicycloorthobenzoate (TBOB) binding site.

The disclosure is also related with treating a disorder responsive to the blockade of calcium channels in mammals suffering from excess activity of said channels by administering an effective amount of a compound of Structure (I) as described herein.

A further aspect of the present disclosure is to provide a method for treating, preventing or ameliorating neuronal loss following global and focal ischemia; treating, preventing or ameliorating ischemia-reperfusion injury; treating, preventing or ameliorating cognitive disorders; treating, preventing or ameliorating convulsion and neurodegenerative conditions; treating, preventing or ameliorating pain including acute and chronic pain, and neuropathic pain; treating, preventing or ameliorating depression; using as anesthetics and antiarrhythmics by administering a compound of Structure (I) to a mammal in need of such treatment or use.

Another aspect of the present disclosure is directed to the use of the indoloquinoline compounds of Structure (I) as calcium channels blockers.

The present disclosure is also directed to the use of a compound of Structure (I) for the treatment of neuronal damage, particularly for the treatment of stroke or brain injury, hemorrhage with tissue injury, chronic neurodegenerative disease such as Alzheimer's disease, Parkinson's disease, Huntington's disease or amyotrophic lateral sclerosis (ALS), epilepsy, convulsive disorder, pain, anxiety, depression, schizophrenia, post-anesthesia cognitive decline, opioid tolerance, drug abuse, alcohol abuse, or the like in mammalian, especially humans.

Also, an aspect of the present disclosure is to provide a pharmaceutical composition useful for treating disorders responsive to the blockade of calcium ion channels, containing an effective amount of a compound of Structure (I) and pharmaceutically acceptable salts and complexes thereof.

DETAILED DESCRIPTION

The present disclosure features calcium channel blockers. "Calcium channel blockers" refer to the compounds able to block calcium channels. The ability of a compound to "block calcium channels" means that the compound prevents a major pathway of calcium entry into depolarized cells through voltage-gated calcium channels.

The use of calcium channel blockers to block calcium channels and/or achieve a beneficial effect in a patient is described below. Also described below are techniques which can be used to obtain additional calcium channel blockers.

Examples of the featured calcium channel blockers representing 2,3,4,7-tetrahydroindolo[2,3-c]quinolines are provided by the chemical formula depicted in Structure (I) and the accompanying description:

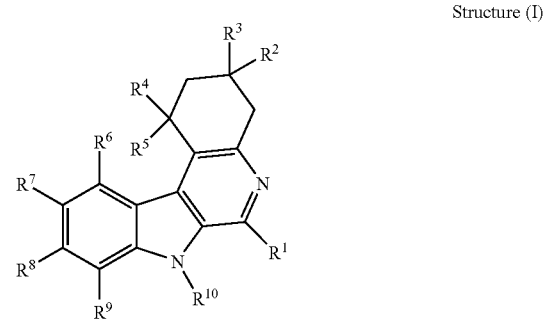

Structure (I)

wherein:

$R^1$ is one of: H, lower alk, cycloalk, aryl, arylalkyl. Preferably, $R^1$ is H or lower alkyl.

$R^2$ and $R^3$ is each independently selected from one of: H, lower alkyl, cycloalk, aryl, arylalkyl; or $R^2$ and $R^3$ are together —$(CH_2)_n$— and n is 6, 5 or 4; or $R^2$ and $R^3$ are together —CH(lower alkyl)$(CH_2)_n$— and n is 5, 4 or 3. Preferably, $R^2$ and $R^3$ is each independently selected from one of: H, lower alkyl, aryl or arylalkyl; or $R^2$ and $R^3$ are together —$(CH_2)_n$— and n is 6, 5 or 4. More preferably, $R^2$ and $R^3$ is each independently selected from one of: H, lower alkyl or aryl; or $R^2$ and $R^3$ are together —$(CH_2)_n$— and n is 5 or 4;

$R^4$ and $R^5$ is each independently selected from one of: H, $NH_2$, OH or lower alk; or $R^4$ and $R^5$ are together O, S or NOH. Preferably, $R^4$ and $R^5$ is each independently selected from one of: H or OH; or $R^4$ and $R^5$ are together O or NOH;

$R^6$, $R^7$, $R^8$, and $R^9$ is each independently selected from the group consisting of: H, halogen, CN, $CF_3$, $OCF_3$, lower alkyl, cycloalk, lower alkoxy, NH-lower alkyl, NH-alkylaryl, N(lower alkyl)$_2$, C(O)OH, C(O)O-lower alkyl, OH, OC(O)-lower alkyl. Preferably, $R^6$, $R^7$, $R^8$, and $R^9$ is each independently selected from the group consisting of: H, halogen, CN, $CF_3$, $OCF_3$, lower alkyl, lower alkoxy;

$R^{10}$ is one of: H, lower alkyl, cycloalk, arylalkyl, aryl. Preferably, $R^{10}$ is selected from one of: H, lower alkyl or arylalkyl;

and pharmaceutically acceptable salts, hydrates, tautomers, solvates and complexes thereof.

"Independently selected," with reference to functional groups (such as $R^2$, $R^3$, $R^4$, $R^5$, $R^6$, $R^7$, $R^8$, $R^9$) means that the functional groups may be selected to be different or the same as each other.

"Alk" refers to either alkyl or alkenyl. "Lower alk" refers to either lower alkyl or lower alkenyl, preferably lower alkyl.

"Alkenyl" refers to an optionally substituted hydrocarbon group containing at least one carbon-carbon double bond between the carbon atoms and containing 2-6 carbon atoms joined together. The alkenyl hydrocarbon group may be straight-chain. Straight-chain alkenyl preferably has 2 to 4 carbons.

"Alkyl" refers to an optionally substituted hydrocarbon group joined by single carbon-carbon bonds and having 1 to 6 carbon atoms joined together. The alkyl hydrocarbon group may be straight-chain or contain one or more branches. Branched- and straight-chain alkyl preferably have 1 to 4 carbons, each of which may be optionally substituted. Alkyl substituents are each independently selected from the group consisting of: lower alkyl, unsubstituted aryl, OH, $NH_2$, NH-lower alkyl, and N(lower alkyl)$_2$. Preferably, no more than two substituents are present. Even more preferably, alkyl is a lower alkyl which is unsubstituted branched- or straight-chain alkyl having 2 to 4 carbons.

"Cycloalk" refers to an optionally substituted cyclic alkyl or an optionally substituted non-aromatic cyclic alkenyl and includes monocyclic and multiple ring structures such as bicyclic and tricyclic. The cycloalkyl has 3 to 15 carbon atoms. Preferably, cycloalkyl has 3 to 6 carbon atoms. Optional substituents for cycloalk are independently selected from the group described above for alkyl and alkenyl.

"Aryl" refers to an optionally substituted aromatic group with at least one ring having a conjugated or fused ring system. Aryl includes carbocyclic aryl, heterocyclic aryl and biaryl groups, all of which may be optionally substituted. Preferably, the aryl is either optionally substituted phenyl.

"Arylalkyl" refers to an aryl-($C_1$-$C_6$)alkyl substituent wherein the alkyl group is linear such as benzyl or phenethyl; or branched. The alkyl portion bonds at the point of attachment to the parent molecule.

"Alkoxy" refers to oxygen joined to an unsubstituted alkyl 1 to 4 carbon atoms in length, preferably 1 to 2 carbons in length. More preferably, the alkoxy is methoxy.

"Halogen" refers to fluorine, chlorine, bromine or iodine. Preferably, the halogen is fluorine or chlorine.

The indoloquinoline compound of Structure (I) may contain one or more asymmetric carbon atoms and may exist in racemic and optically active forms. All of these compounds and diastereomers are contemplated to be within the scope of the present invention.

Compounds which are particularly useful embodiments include:
9-fluoro-3,3,6-trimethyl-2,3,4,7-tetrahydroindolo[2,3-c]quinolin-1-one;
10-methoxy-3,3,6-trimethyl-2,3,4,7-tetrahydroindolo[2,3-c]quinolin-1-one;
11-fluoro-3,3,6-trimethyl-2,3,4,7-tetrahydroindolo[2,3-c]quinolin-1-one;
6-methyl-3'H-spirocyclohexane-2,3,4,7-tetrahydroindolo[2,3-c]quinolin-1-one;

An expanded list of compounds which are particularly useful embodiments include:
9-fluoro-3,3,6-trimethyl-2,3,4,7-tetrahydroindolo[2,3-c]quinolin-1-one;
3,3,6-trimethyl-2,3,4,7-tetrahydroindolo[2,3-c]quinolin-1-one;
10-methoxy-3,3,6-trimethyl-2,3,4,7-tetrahydroindolo[2,3-c]quinolin-1-one;
11-fluoro-3,3,6-trimethyl-2,3,4,7-tetrahydroindolo[2,3-c]quinolin-1-one;
6-methyl-3'H-spirocyclohexane-2,3,4,7-tetrahydroindolo[2,3-c]quinolin-1-one;
10-chloro-3,3,6-trimethyl-2,3,4,7-tetrahydroindolo[2,3-c]quinolin-1-one;
6-ethyl-3,3-dimethyl-2,3,4,7-tetrahydro-indolo[2,3-c]quinolin-1-one.

A more expanded list of compounds which are particularly useful embodiments include:
3,3-dimethyl-2,3,4,7-tetrahydroindolo[2,3-c]quinolin-1-one;
9-fluoro-3,3,6-trimethyl-2,3,4,7-tetrahydroindolo[2,3-c]quinolin-1-one;
3,3,6-trimethyl-2,3,4,7-tetrahydroindolo[2,3-c]quinolin-1-one;
10-methoxy-3,3-dimethyl-2,3,4,7-tetrahydroindolo[2,3-c]quinolin-1-one;
10-methoxy-3,3,6-trimethyl-2,3,4,7-tetrahydroindolo[2,3-c]quinolin-1-one;
11-fluoro-3,3,6-trimethyl-2,3,4,7-tetrahydroindolo[2,3-c]quinolin-1-one;
3-isopropyl-6-methyl-2,3,4,7-tetrahydroindolo[2,3-c]quinolin-1-one;
6-methyl-3'H-spirocyclohexane-2,3,4,7-tetrahydroindolo[2,3-c]quinolin-1-one;
10-chloro-3,3,6-trimethyl-2,3,4,7-tetrahydroindolo[2,3-c]quinolin-1-one;
9,10-difluoro-3,3,6-trimethyl-2,3,4,7-tetrahydroindolo[2,3-c]quinolin-1-one;
6-ethyl-3,3-dimethyl-2,3,4,7-tetrahydro-indolo[2,3-c]quinolin-1-one;
10-fluoro-3,3,6-trimethyl-2,3,4,7-tetrahydroindolo[2,3-c]quinolin-1-one;
3,3,6-trimethyl-2,3,4,7-tetrahydro-1H-indolo[2,3-c]quinoline.

A further expanded list of the compounds include:
3,3-dimethyl-2,3,4,7-tetrahydroindolo[2,3-c]quinolin-1-one;
3,3-dimethyl-2,3,4,7-tetrahydroindolo[2,3-c]quinoline;
9-fluoro-3,3,6-trimethyl-2,3,4,7-tetrahydroindolo[2,3-c]quinolin-1-one;
3,3,6-trimethyl-2,3,4,7-tetrahydroindolo[2,3-c]quinolin-1-one;
9-fluoro-3,3-dimethyl-2,3,4,7-tetrahydroindolo[2,3-c]quinolin-1-one;
10-methoxy-3,3-dimethyl-2,3,4,7-tetrahydroindolo[2,3-c]quinolin-1-one;
10-methoxy-3,3,6-trimethyl-2,3,4,7-tetrahydroindolo[2,3-c]quinolin-1-one;
9-chloro-3,3,6-trimethyl-2,3,4,7-tetrahydroindolo[2,3-c]quinolin-1-one;
9-methoxy-3,3,6-trimethyl-2,3,4,7-tetrahydroindolo[2,3-c]quinolin-1-one;
11-fluoro-3,3,6-trimethyl-2,3,4,7-tetrahydroindolo[2,3-c]quinolin-1-one;
3,6-dimethyl-2,3,4,7-tetrahydroindolo[2,3-c]quinolin-1-one;

3-isopropyl-6-methyl-2,3,4,7-tetrahydroindolo[2,3-c]quinolin-1-one;
6-methyl-3'H-spirocyclohexane-2,3,4,7-tetrahydroindolo[2,3-c]quinolin-1-one;
10-chloro-3,3,6-trimethyl-2,3,4,7-tetrahydroindolo[2,3-c]quinolin-1-one;
6-methyl-3-phenyl-2,3,4,7-tetrahydroindolo[2,3-c]quinolin-1-one;
3,3,6-trimethyl-2,3,4,7-tetrahydroindolo[2,3-c]quinolin-1-one oxime;
3,6-dimethyl-2,3,4,7-tetrahydroindolo[2,3-c]quinolin-1-one oxime;
9,10-difluoro-3,3,6-trimethyl-2,3,4,7-tetrahydroindolo[2,3-c]quinolin-1-one;
6-ethyl-3,3-dimethyl-2,3,4,7-tetrahydro-indolo[2,3-c]quinolin-1-one;
10-fluoro-3,3,6-trimethyl-2,3,4,7-tetrahydroindolo[2,3-c]quinolin-1-one;
3,3,6-trimethyl-2,3,4,7-tetrahydro-1H-indolo[2,3-c]quinoline;
7-N-ethyl-3,3,6-trimethyl-2,3,4,7-tetrahydroindolo[2,3-c]quinolin-1-one.

An even more expanded list of the compounds include:
3,3-dimethyl-2,3,4,7-tetrahydroindolo[2,3-c]quinolin-1-one;
3,3-dimethyl-2,3,4,7-tetrahydroindolo[2,3-c]quinoline;
9-fluoro-3,3,6-trimethyl-2,3,4,7-tetrahydroindolo[2,3-c]quinolin-1-one;
3,3,6-trimethyl-2,3,4,7-tetrahydroindolo[2,3-c]quinolin-1-one;
9-fluoro-3,3-dimethyl-2,3,4,7-tetrahydroindolo[2,3-c]quinolin-1-one;
10-methoxy-3,3-dimethyl-2,3,4,7-tetrahydroindolo[2,3-c]quinolin-1-one;
10-methoxy-3,3,6-trimethyl-2,3,4,7-tetrahydroindolo[2,3-c]quinolin-1-one;
9-chloro-3,3-dimethyl-2,3,4,7-tetrahydroindolo[2,3-c]quinolin-1-one;
9-chloro-3,3,6-trimethyl-2,3,4,7-tetrahydroindolo[2,3-c]quinolin-1-one;
9-methoxy-3,3,6-trimethyl-2,3,4,7-tetrahydroindolo[2,3-c]quinolin-1-one;
11-fluoro-3,3,6-trimethyl-2,3,4,7-tetrahydroindolo[2,3-c]quinolin-1-one;
3,6-dimethyl-2,3,4,7-tetrahydroindolo[2,3-c]quinolin-1-one;
3-isopropyl-6-methyl-2,3,4,7-tetrahydroindolo[2,3-c]quinolin-1-one;
6-methyl-3'H-spirocyclohexane-2,3,4,7-tetrahydroindolo[2,3-c]quinolin-1-one;
10-chloro-3,3,6-trimethyl-2,3,4,7-tetrahydroindolo[2,3-c]quinolin-1-one;
6-methyl-3-phenyl-2,3,4,7-tetrahydroindolo[2,3-c]quinolin-1-one;
3,3,6-trimethyl-2,3,4,7-tetrahydroindolo[2,3-c]quinolin-1-one oxime;
3,6-dimethyl-2,3,4,7-tetrahydroindolo[2,3-c]quinolin-1-one oxime;
9,10-difluoro-3,3,6-trimethyl-2,3,4,7-tetrahydroindolo[2,3-c]quinolin-1-one;
6-ethyl-3,3-dimethyl-2,3,4,7-tetrahydro-indolo[2,3-c]quinolin-1-one;
6-isopropyl-3,3-dimethyl-2,3,4,7-tetrahydroindolo[2,3-c]quinolin-1-one;
10-fluoro-3,3,6-trimethyl-2,3,4,7-tetrahydroindolo[2,3-c]quinolin-1-one;
3,3,6-trimethyl-2,3,4,7-tetrahydro-1H-indolo[2,3-c]quinoline;
7-N-ethyl-3,3,6-trimethyl-2,3,4,7-tetrahydroindolo[2,3-c]quinolin-1-one;
7-N-propyl-3,3,6-trimethyl-2,3,4,7-tetrahydroindolo[2,3-c]quinolin-1-one.

Pharmaceutically acceptable salts are non-toxic salts in the amounts and concentrations at which they are administered.

Pharmaceutically acceptable salts include acid addition salts such as those containing sulfate, hydrochloride, fumarate, maleate, phosphate, sulfamate, acetate, citrate, lactate, tartrate, methanesulfonate, ethanesulfonate, benzenesulfonate, p-toluenesulfonate, cyclohexylsulfamate and quinate. Hydrochloride is particularly useful pharmaceutically acceptable salt. Pharmaceutically acceptable salts can be obtained from acids such as hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, cyclohexylsulfamic acid, fumaric acid and quinic acid.

Pharmaceutically acceptable salts also include basic addition salts such as those containing benzathine, chloroprocaine, choline, diethanolamine, ethylenediamine, meglumine, procaine, aluminum, calcium, lithium, magnesium, potassium, sodium, ammonium, alkylamine, and zinc, when acidic functional groups, such as alcohol, phenol of carboxylic acid are present.

By way of example, the calcium channel blockers of Structure (I) wherein $R^1$ is hydrogen or lower alkyl, $R^4$ and $R^5$ together are oxygen, and $R^{10}$ is hydrogen, can be prepared according to Scheme I involving a method of reacting an appropriate 1-oxo-2,3,4,7-tetrahydro-1H-5-oxonia-7-azabenzo[c]fluorene with ammonia hydroxide in isopropanol, or with ammonia acetate in water.

The calcium channel blockers of Structure (I) wherein $R^1$ is hydrogen or lower alkyl, and $R^4$, $R^5$ and $R^{10}$ is each hydrogen, can be prepared according to Scheme I by reduction of an appropriate 2,3,4,7-tetrahydroindolo[2,3-c]quinolin-1-one of Structure (I) involving a method of reacting an appropriate 2,3,4,7-tetrahydroindolo[2,3-c]quinolin-1-one with hydrazine hydrate in ethylene glycol.

The calcium channel blockers of Structure (I) wherein $R^1$ is hydrogen or lower alkyl, $R^4$ and $R^5$ together are the N-hydroxylamino group, and $R^{10}$ is hydrogen, can be prepared according to Scheme I involving a method of reacting an appropriate 2,3,4,7-tetrahydroindolo[2,3-c]quinolin-1-one of Structure (I) with hydroxylamine hydrochloride in pyridine and ethanol.

The calcium channel blockers of Structure (I) wherein $R^1$ is hydrogen or lower alkyl, $R^4$ and $R^5$ together are oxygen, and $R^{10}$ is lower alkyl, can be prepared according to Scheme I by alkylation of an appropriate 2,3,4,7-tetrahydroindolo[2,3-c]quinolin-1-one of Structure (I) involving a method of reacting an appropriate 2,3,4,7-tetrahydroindolo[2,3-c]quinolin-1-one with sodium hydride and alkyl halide in anhydrous N,N-dimethylformamide.

The 1-oxo-2,3,4,7-tetrahydro-1H-5-oxonia-7-azabenzo[c]fluorenes can be prepared according to Scheme I involving a method of reacting an appropriate 2-(1H-indol-3-yl)cyclohexane-1,3-dione with an appropriate carboxylic acid anhydride and perchloric acid or phosphorous acid, or with diethoxymethoxyethane and tetrafluoroboric acid.

The 2-(1H-indol-3-yl)cyclohexane-1,3-diones can be prepared according to Scheme I involving a method of reacting an appropriate 2-(1-acetyl-1H-indol-3-yl)cyclohexane-1,3-dione with sodium hydroxide.

The 2-(1-acetyl-1H-indol-3-yl)cyclohexane-1,3-diones can be prepared according to Scheme I involving a method of reacting an appropriate 1-acetyl-1,2-dihydroindol-3-one with an appropriate cyclohexane-1,3-dione and triethylamine in acetic acid.

The 1-acetyl-1,2-dihydroindol-3-ones can be prepared according to Scheme I involving a method of reacting an appropriate acetic acid 1-acetyl-1H-indol-3-yl ester with sodium sulfite in water.

The acetic acid 1-acetyl-1H-indol-3-yl esters can be prepared according to Scheme I involving a method of reacting an appropriate 2-(N-acetylcarboxymethylamino)benzoic acid and acetic anhydride.

The 2-(N-acetylcarboxymethylamino)benzoic acids can be prepared involving a method of reacting an appropriate 2-(carboxymethylamino)benzoic acid with sodium carbonate and acetic anhydride using standard techniques.

The 2-(carboxymethylamino)benzoic acids can be prepared involving a method of reacting an appropriate 2-aminobenzoic acid and chloroacetic acid using standard techniques [see, for example, S. Holt, et al., Proc. Roy. Soc. B 148: 481-494 (1958); S. Holt, et al., J. Chem. Soc. 1217-1223 (1958); E. Tighineanu, et al., Tetrahedron 36: 1385-1397 (1980); V. I. Dulenko, et al., Chem. Heterocycl. Comp. (Engl. Transl.) 3: 302-305 (1985); I. V. Komissarov, et al., Chem. Heterocycl. Comp. (Engl. Transl.) 19: 187-191 (1986); I. V. Komissarov, et al., Chem. Heterocycl. Comp. (Engl. Transl.) 23: 471-474 (1989); M. Kollmar, et al., Org. Synth. Coll. Vol. 10: 23 (2004)].

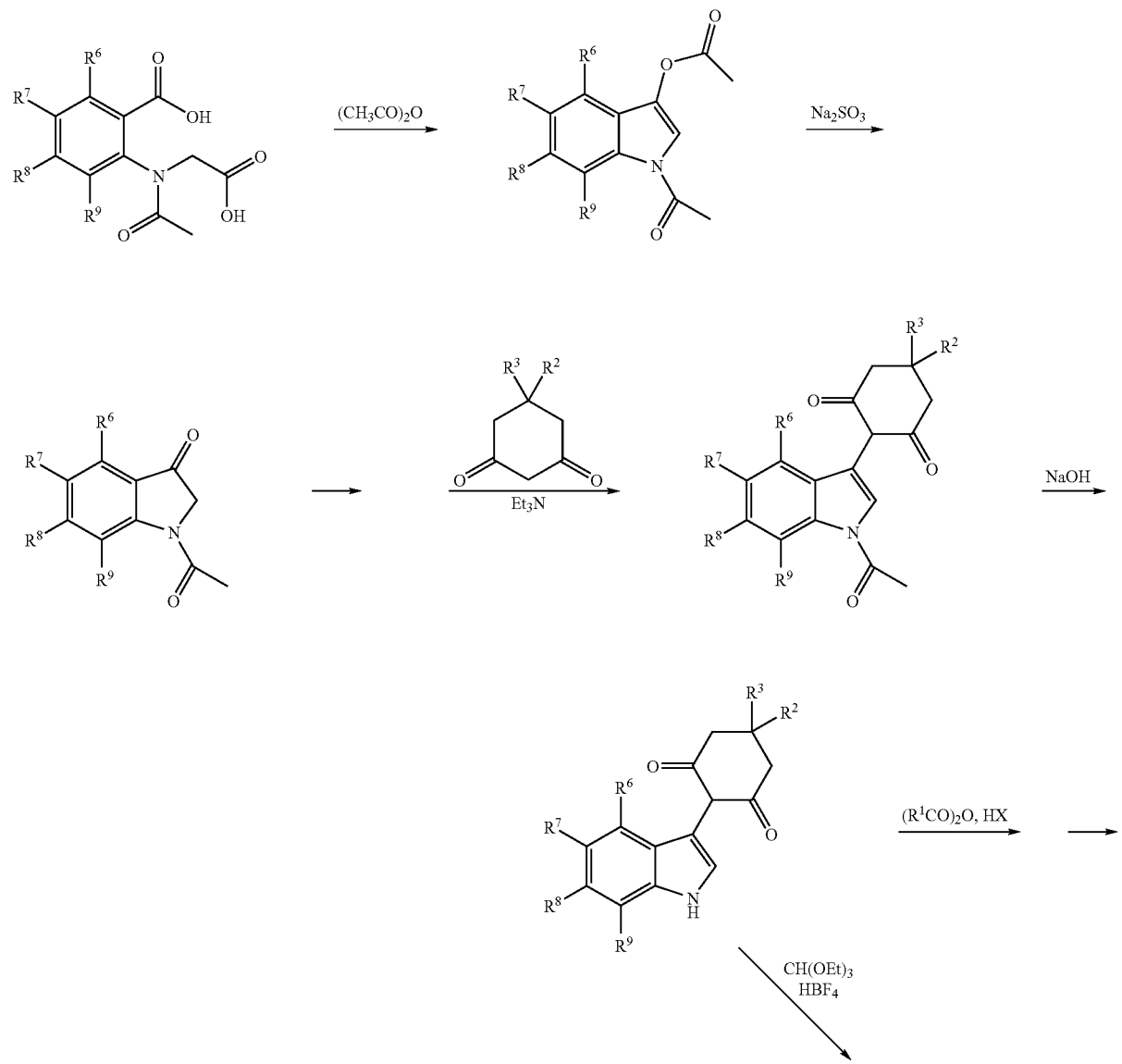

Scheme I

-continued

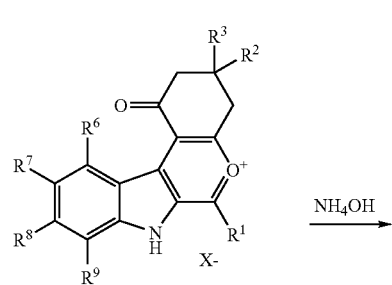 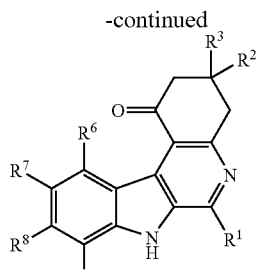 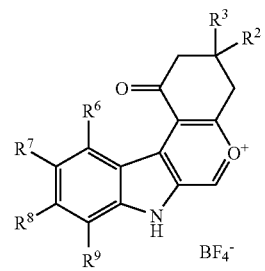

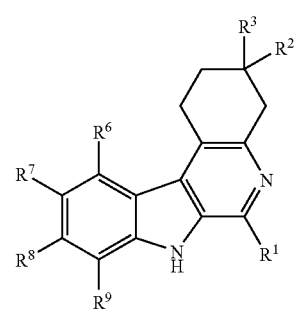 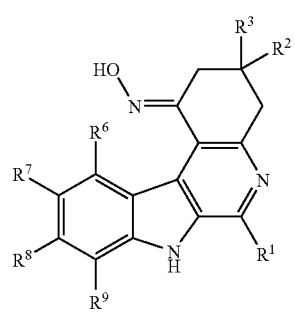 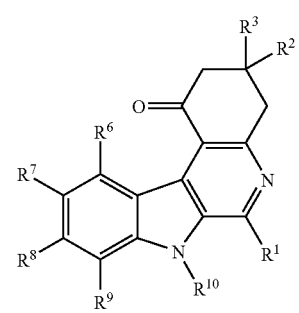

In order to use a compound of Structure (I) or a pharmaceutically acceptable salt or complex thereof for the treatment of humans and other mammals, it is normally formulated in accordance with standard pharmaceutical practice as a pharmaceutical composition.

The calcium channel blockers can be administered by different routes including intravenous, intraperitoneal, subcutaneous, intramuscular, oral, topical (transdermal), or transmucosal administration. For systemic administration, oral administration is preferred. For oral administration, for example, the compounds can be formulated into conventional oral dosage forms such as capsules, tablets, and liquid preparations such as syrups, elixirs, and concentrated drops.

Alternatively, injection (parenteral administration) may be used, e.g., intramuscular, intravenous, intraperitoneal, and subcutaneous. For injection, the compounds of the invention are formulated in liquid solutions, preferably, in physiologically compatible buffers or solutions, such as saline solution, Hank's solution, or Ringer's solution. In addition, the compounds may be formulated in solid form and redissolved or suspended immediately prior to use. Lyophilized forms can also be produced.

Systemic administration can also be achieved by transmucosal or transdermal methods. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration, for example, may be through nasal sprays, rectal suppositories, or vaginal suppositories.

For topical administration, the compounds of the invention can be formulated into ointments, salves, gels, or creams, as is generally known in the art.

The amounts of various calcium channel blockers to be administered can be determined by standard procedures taking into account factors such as the compound $IC_{50}$, $EC_{50}$, the biological half-life of the compound, the age, size and weight of the patient, and the disease or disorder associated with the patient. The importance of these and other factors to be considered are known to those of ordinary skill in the art.

Amounts administered also depend on the routes of administration and the degree of oral bioavailability. For example, for compounds with low oral bioavailability, relatively higher doses may have to be administered.

The composition may be in unit dosage form. For oral application, for example, a tablet or capsule may be administered, for nasal application, a metered aerosol dose may be administered, for transdermal application, a topical formulation or patch may be administered, and for transmucosal delivery, a buccal patch may be administered. In each case, dosing is such that the patient may administer a single dose.

Each dosage unit for oral administration contains suitably from 0.01 to 500 mg/kg, and preferably from 0.1 to 50 mg/kg, of a compound of Structure (I) or a pharmaceutically acceptable salt or complex thereof, calculated as the free base. The daily dosage for parenteral, nasal, oral inhalation, transmucosal or transdermal routes contains suitably from 0.01 mg to 100 mg/kg, of a compound of Structure (I). A topical formulation contains suitably 0.01 to 5.0% of a compound of Structure (I). The active ingredient may be administered as a single dose or in multiple doses, for example, from 2 to 6 times per day, sufficient to exhibit the desired activity, as is readily apparent to one skilled in the art.

As used herein, "treatment" of a disease includes, but is not limited to prevention, retardation and prophylaxis of the disease.

Diseases and disorders which might be treated or prevented, based upon the affected cells, include the central nervous system diseases or disorders such as seizures, stroke, head trauma, spinal cord injury, hemorrhage with tissue injury, hypoxia-induced nerve cell damage, such as occurs in cardiac arrest or neonatal distress, epilepsy, neurodegenerative diseases such as Alzheimer's disease, Huntington's disease and Parkinson's disease, dementia, muscle tension, pain, depression, anxiety, panic disorder, obsessive-compulsive disorder, post-traumatic stress disorder, post-anesthesia cognitive decline, opioid tolerance, drug abuse, alcohol abuse, schizophrenia, neuroleptic malignant syndrome, and Tourette's syndrome; diseases involving excess water reabsorption by the kidney, such as syndrome of inappropriate ADH secretion (SIADH), cirrhosis, congestive heart failure, and nephrosis; hypertension; preventing and/or decreasing renal toxicity from cationic antibiotics (e.g., aminoglycoside antibiotics); gut motility disorders such as diarrhea and spastic colon; GI ulcer diseases; GI diseases with excessive calcium absorption such as sarcoidosis; autoimmune diseases and organ transplant rejection; squamous cell carcinoma; and pancreatitis.

Composition of Structure (I) and their pharmaceutically acceptable salts and/or complexes, which are active when given orally, can be formulated as syrups, tablets, capsules, and lozenges. A syrup formulation will generally consist of a suspension or solution of the compound or salt in a liquid carrier such as, for example, ethanol, peanut oil, olive oil, glycerine or water with a flavoring or coloring agent. Where the composition is in the form of a tablet, any pharmaceutical carrier routinely used for preparing solid formulations may be used. Examples of such carriers include magnesium stearate, terra alba, talc, gelatin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule, any pharmaceutical carrier routinely used for preparing dispersions or suspensions may be utilized. For example, aqueous gums, celluloses, silicates or oils may be used to form a soft gelatin capsule shell.

Typical parenteral compositions consist of a solution or suspension of a compound or salt in a sterile aqueous or non-aqueous carrier optionally containing parenterally acceptable oil, for example polyethylene glycol, polyvinylpyrrolidone, lecithin, arachis oil or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Structure (I) or a pharmaceutically acceptable salt or complex thereof which is active when administered in this way, with a binding and/or lubricating agent, for example polymeric glycols, gelatins, cocoa-butter or other low-melting vegetable waxes or fats or their synthetic analogs.

Typical dermal and transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer a single dose.

No unacceptable toxological effects are expected when compounds of the present invention are administered in accordance with the present invention.

EXAMPLES

The following specific examples are included for illustrative purposes only and are not to be considered as limiting to this disclosure. The reagents and intermediates used in the following examples are either commercially available or can be prepared according to standard literature procedures by those skilled in the art of organic synthesis.

NMR (Nuclear Magnetic Resonance) spectroscopy was performed on a Varian Gemini 300 spectrometer. Proton spectra were recorded at 300 MHz in deuterochloroform ($CDCl_3$), dimethylsulfoxide-$d_8$ (DMSO-$d_6$) or trifluoroacetic acid ($CF_3COOH$) solutions. NMR resonances are reported in δ (ppm) relative to tetramethylsilane (TMS) as internal standard with the following descriptors for the observed multiplicities: s (singlet), d (doublet), t (triplet), q (quartet), dd (doublet of doublets), and m (multiplet).

Example 1

Preparation of 3,3-dimethyl-2,3,4,7-tetrahydroindolo[2,3-c]quinolin-1-one a) 2-(Carboxymethylamino)benzoic acid

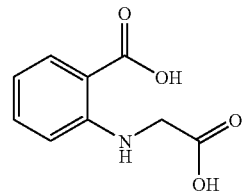

To a solution of chloroacetic acid (347 g, 3.67 mol) in water (500 mL), sodium carbonate (200 g, 4.72 mol) was carefully added at room temperature under stirring. The formed solution was heated to 40-45° C. and quickly added to a mixture prepared from a suspension of anthranilic acid (500 g, 3.65 mol) in water (340 mL) and 35% aqueous sodium hydroxide solution (320 mL) and heated to 40-45° C. The reaction mixture was kept at 40° C. for 4 days and the solid reaction mixture was treated with a solution of sodium hydroxide (150 g, 3.75 mol) in water (4 L). The mixture was heated to 60° C. and filtered off while hot. The solid residue was washed on the filter with 20% aqueous sodium hydroxide until the solid residue was dissolved, and the combined filtrates were acidified with 37% aqueous hydrochloric acid to pH 3. The precipitate was filtered off; an additional amount of the product precipitated overnight from the filtrate and was collected. The product was dried at 100° C. to give total 567 g (80%), m.p. 220° C.

b) 2-(N-Acetylcarboxymethylamino)benzoic acid

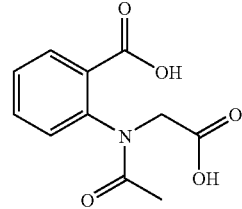

To a solution of sodium carbonate (89 g, 0.84 mol) in water (830 mL), 2-(carboxymethylamino)benzoic acid of Example 1a (100 g, 0.84 mol) was added in small portions at room temperature under stirring while a clear solution was formed. Acetic anhydride (85.68 g, 0.84 mol) was added dropwise at room temperature under stirring. The reaction mixture was stirred for 30 min, and 37% aqueous hydrochloric acid (140 mL) was added dropwise. The product precipitated slowly. The solid product was filtered off in 12 h, washed with water (3×150 mL) and air-dried to afford 110 g (91%), m.p. 206° C.

c) Acetic acid 1-acetyl-1H-indol-3-yl ester

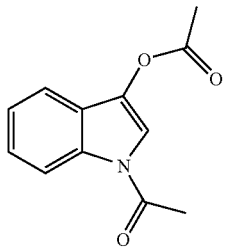

To a stirred mixture of acetic anhydride (46.29 g, 0.45 mol) and triethylamine (13.77 g, 0.14 mol), 2-(N-acetylcarboxymethylamino)benzoic acid of Example 1b (11.36 g, 0.048 mol) was added at room temperature. The mixture was refluxed for 20 min and concentrated in vacuum to give an oily residue. Water (350 mL) was added under vigorous stirring, and the mixture was refrigerated overnight. The solid product was collected, washed with water and air-dried to give 9.0 g (86%) of the product which was used in the next step without purification.

d) 1-Acetyl-1,2-dihydroindol-3-one

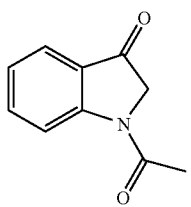

A solution of sodium sulfite (12.6 g, 0.1 mol) in water (180 mL) was heated to 70-75° C. under stirring, and the acetic acid 1-acetyl-1H-indol-3-yl ester of Example 1c (9.0 g, 0.041 mol) was added in small portions. The mixture was stirred at 70-75° C. for 1.5 h, and then kept at room temperature overnight. The solid product was filtered off, dried, dissolved in methylene chloride (40 mL) and flash-chromatographed on aluminum oxide with methylene chloride as an eluent to give 5.25 g (71%) of light yellow product; m.p. 138° C.

e) 2-(1-Acetyl-1H-indol-3-yl)-5,5-dimethylcyclohexane-1,3-dione

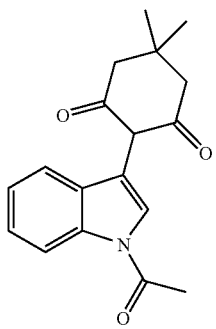

1-Acetyl-1,2-dihydroindol-3-one of Example 1d (131.3 g, 0.75 mol) and 5,5-dimethyl-cyclohexane-1,3-dione (105 g, 0.75 mol) were added to a mixture of acetic acid (700 mL) and triethylamine (105 mL, 0.75 mol) at room temperature under stirring. The reaction mixture was refluxed for 6 h. About ⅓ volume of solvents was removed in vacuum, and the mixture was cooled and diluted with water (50 mL). The precipitate was filtered off, washed with ethanol-water, 1:1 and dried to afford 169.4 g (76%) of colorless crystals; m.p. 225-227° C.

f) 2-(1H-Indol-3-yl)-5,5-dimethylcyclohexane-1,3-dione

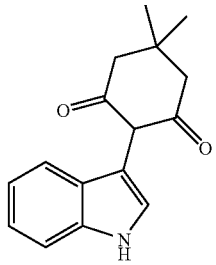

To a mixture of 2-(1-acetyl-1H-indol-3-yl)-5,5-dimethylcyclohexane-1,3-dione of Example 1e (74.8 g, 0.25 mol) and methanol (30 mL), a solution of sodium hydroxide (30 g, 0.75 mol) in water (300 mL) was added at room temperature under stirring. The reaction mixture was heated at 60° C. for 2 h under stirring, and then activated charcoal (10 g) and water (300 mL) were added. The mixture was stirred for 10 min, charcoal was filtered off, and the filtrate was acidified with hydrochloric acid to pH 2. The solid product was filtered off, washed with water and dried to give 38.3 g (60%) of the colorless solid; m.p. 173° C.

g) 3,3-Dimethyl-1-oxo-2,3,4,7-tetrahydro-1H-5-oxonia-7-azabenzo[c]fluorene tetrafluoroborate

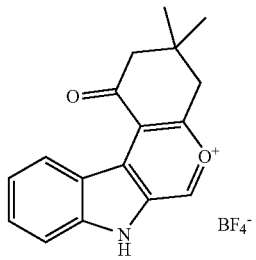

To a suspension of 2-(1H-indol-3-yl)-5,5-dimethylcyclohexane-1,3-dione of Example 1f (2.5 g, 9.8 mmol) in diethoxymethoxyethane (20 mL), tetrafluoroboric acid (54 wt % solution in diethyl ether, 2 mL, 14.5 mmol) was added in two portions under stirring. The mixture was stirred at room temperature for 2 h and diluted with diethyl ether (20 mL). The solid product was filtered off, washed with diethyl ether and air-dried at room temperature to give 2.4 g (70%) of the product as red crystals, which was used in the next step without purification.

h) 3,3-Dimethyl-2,3,4,7-tetrahydroindolo[2,3-c]quinolin-1-one

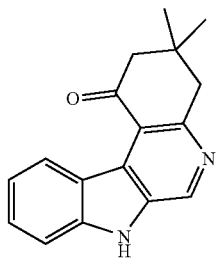

To a mixture of 3,3-dimethyl-1-oxo-2,3,4,7-tetrahydro-1H-5-oxonia-7-azabenzo[c]fluorene tetrafluoroborate of Example 1g (2.4 g; 6.8 mmol) and acetic acid (35 mL) was added ammonium acetate (30 g), and the mixture was refluxed for 30 min. The reaction mixture was cooled, water (40 mL) added, and then aqueous solution of ammonium hydroxide was added to pH 9. The solid product was filtered off, washed with water and air-dried at room temperature. The product was dissolved in the mixture of ethanol (15 mL) and diethyl ether (15 mL) at room temperature, and 37% aqueous hydrochloric acid (0.72 mL) was added dropwise. The mixture was kept at room temperature for 2 h. The crystalline product was filtered off, washed with ethanol-diethyl ether, 1:3 (2 mL), then with diethyl ether and dried to give 1.64 g of colorless crystals. This product was dissolved in water (30 mL) and aqueous ammonium hydroxide was added to pH 9. The precipitate was filtered off, washed with water, dried and crystallized from toluene to give 1.4 g (78%) of colorless crystals; m.p. 224-225° C. $^1$H NMR (DMSO-$d_6$): δ 1.09 (s, 6H), 2.70 (s, 2H), 3.16 (s, 2H), 7.22-7.25 (m, 1H), 7.59-7.62 (m, 2H), 9.05 (s, 1H), 9.22 (d, 1H), 11.96 (s, 1H).

Example 2

Preparation of 3,3-dimethyl-2,3,4,7-tetrahydroindolo[2,3-c]quinoline

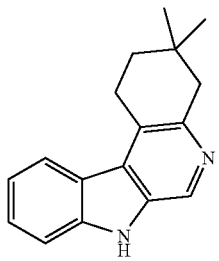

3,3-Dimethyl-2,3,4,7-tetrahydroindolo[2,3-c]quinolin-1-one of Example 1h (1.36 g, 5.14 mmol) was added to a mixture of ethylene glycol (8 mL) and hydrazine monohydrate (5 mL) at room temperature under stirring. The mixture was refluxed for 1 h, cooled, potassium hydroxide (1 g) was added, and the reaction mixture was refluxed for 2 h. The excess of hydrazine and water was slowly distilled off at 1 psi until the vapor temperature reached 190° C. The residue was cooled, diluted with water (60 mL), and the solid product was filtered off, washed with water and recrystallized from ethanol-water, 1:1. The product was isolated as colorless solid (0.59 g, 46%). Crystallization from toluene yielded the analytically pure sample; m.p. 275-277° C. $^1$H NMR (DMSO-$d_6$) δ 1.03 (s, 6H), 1.72 (t, 2H), 2.76 (s, 2H), 3.30 (t, 2H), 7.20-7.23 (m, 1H), 7.49-7.60 (m, 2H), 8.17 (d, 1H), 8.66 (s, 1H), 11.45 (s, 1H).

Example 3

Preparation of 9-fluoro-3,3,6-trimethyl-2,3,4,7-tetrahydroindolo[2,3-c]quinolin-1-one a) 2-(6-Fluoro-1H-indol-3-yl)-5,5-dimethylcyclohexane-1,3-dione

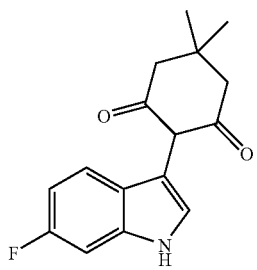

Utilizing the procedures described in Example 1 a-e except substituting 2-amino-4-fluorobenzoic acid for anthranilic acid in step 1a, the title compound was prepared and crystallized from ethanol-water, 1:1.

b) 9-Fluoro-3,3,6-trimethyl-1-oxo-2,3,4,7-tetrahydro-1H-5-oxonia-7-aza-benzo[c]fluorene perchlorate

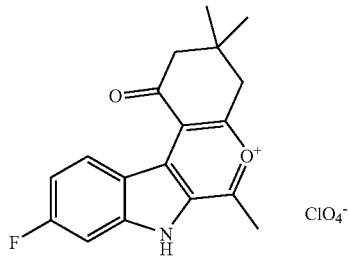

2-(6-Fluoro-1H-indol-3-yl)-5,5-dimethylcyclohexane-1,3-dione of Example 3a (0.575 g, 2.1 mmol) was slowly added at room temperature under stirring to a freshly prepared mixture of acetic acid (2 mL), acetic anhydride (2.1 mL) and 70% aqueous perchloric acid (0.17 mL). The reaction mixture was stirred at room temperature for 4 h, diethyl ether (5 mL) was added, and the product was filtered off, washed with diethyl ether and dried at room temperature to give 0.72 g (89%) of the bright yellow crystals. The product was used in the next step without purification.

c) 9-Fluoro-3,3,6-trimethyl-2,3,4,7-tetrahydroindolo[2,3-c]quinolin-1-one

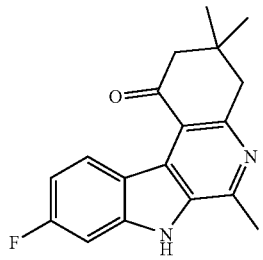

Aqueous ammonium hydroxide solution (3 mL) was added to a suspension of 9-fluoro-3,3,6-trimethyl-1-oxo-2,3,4,7-tetrahydro-1H-5-oxonia-7-aza-benzo[c]fluorene perchlorate of Example 3b (0.72 g, 1.88 mmol) in isopropanol (2 mL). The reaction mixture was refluxed for 1 h, cooled, and water (5 mL) was added. Aqueous ammonium hydroxide solution was added to the mixture to pH 9. The precipitate was filtered off, washed with water and dried. The crude product was dissolved in acetone, and 37% aqueous hydrochloric acid (0.2 mL) was added. The precipitate was filtered off, suspended in hot water, and the mixture was basicified with ammonium hydroxide to pH 9. The product was filtered off, washed with water, dried and crystallized from toluene to give 0.26 g (50%) of colorless crystals; m.p. 244-246° C.

Example 4

Preparation of 3,3,6-trimethyl-2,3,4,7-tetrahydroindolo[2,3-c]quinolin-1-one

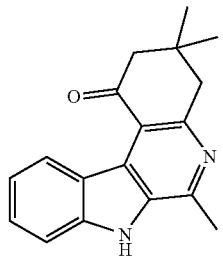

Utilizing the procedures described in Example 3 a-c except substituting 2-(1H-indol-3-yl)-5,5-dimethylcyclohexane-1,3-dione of Example 1f for 2-(6-fluoro-1H-indol-3-yl)-5,5- dimethylcyclohexane-1,3-dione in step 3a, the title compound was prepared and crystallized from toluene; m.p. 176-177° C. ¹H NMR (CF₃COOH): δ 1.3 (s, 6H), 2.07 (s, 2H), 3.17 (s, 3H), 3.37 (s, 2H), 7.33-7.9 (m, 4H), 9.27 (d, 1H).

Example 5

Preparation of 9-fluoro-3,3-dimethyl-2,3,4,7-tetrahydroindolo[2,3-c]quinolin-1-one

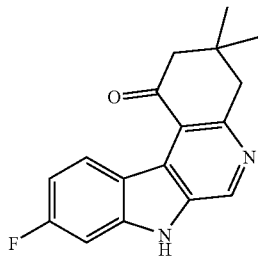

Utilizing the procedures described in Example 1 a-h except substituting 2-amino-4-fluorobenzoic acid for anthranilic acid in step 1a, the title compound was prepared and crystalized toluene; m.p. 271-273° C.

Example 6

Preparation of 10-methoxy-3,3-dimethyl-2,3,4,7-tetrahydroindolo[2,3-c]quinolin-1-one

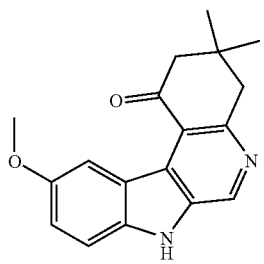

Utilizing the procedures described in Example 1 a-h except substituting 2-amino-5-methoxybenzoic acid for anthranilic acid in step 1a, the title compound was prepared and crystallized from toluene; m.p. 230-231° C.

Example 7

Preparation of 10-methoxy-3,3,6-trimethyl-2,3,4,7-tetrahydroindolo[2,3-c]quinolin-1-one

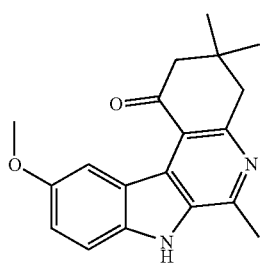

Utilizing the procedures described in Example 3 a-c except substituting 2-(5-methoxy-1H-indol-3-yl)-5,5-dimethylcyclohexane-1,3-dione for 2-(6-fluoro-1H-indol-3-yl)-5,5-dimethylcyclohexane-1,3-dione in step 3a, and 2-amino-5-methoxybenzoic acid for anthranilic acid in step 1a of Example 1, the title compound was prepared and crystallized from toluene; m.p. 241-243° C.

Example 8

Preparation of 9-chloro-3,3-dimethyl-2,3,4,7-tetrahydroindolo[2,3-c]quinolin-1-one

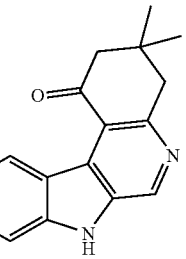

Utilizing the procedures described in Example 1 a-h except substituting 2-amino-4-chlorobenzoic acid for anthranilic acid in step 1a, the title compound was prepared and crystallized from toluene; m.p. 257-259° C.

Example 9

Preparation of 9-chloro-3,3,6-trimethyl-2,3,4,7-tetrahydroindolo[2,3-c]quinolin-1-one

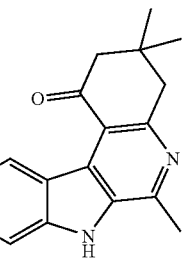

Utilizing the procedures described in Example 3 a-c except substituting 2-(6-chloro-1H-indol-3-yl)-5,5-dimethylcyclohexane-1,3-dione for 2-(6-fluoro-1H-indol-3-yl)-5,5-dimethylcyclohexane-1,3-dione in step 3a, and 2-amino-4-chlorobenzoic acid for anthranilic acid in step 1a of Example 1, the title compound was prepared and crystallized from toluene; m.p. 248-250° C.

Example 10

Preparation of 9-methoxy-3,3,6-trimethyl-2,3,4,7-tetrahydroindolo[2,3-c]quinolin-1-one

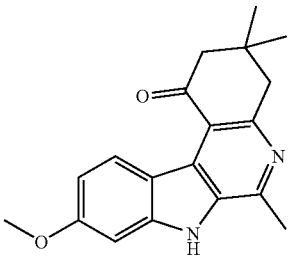

Utilizing the procedures described in Example 3 a-c except substituting 2-(6-methoxy-1H-indol-3-yl)-5,5-dimethylcyclohexane-1,3-dione for 2-(6-fluoro-1H-indol-3-yl)-5,5-dimethylcyclohexane-1,3-dione in step 3a, and 2-amino-4-methoxybenzoic acid for anthranilic acid in step 1a of Example 1, the title compound was prepared and crystallized from toluene; m.p. 250-252° C.

Example 11

Preparation of 11-fluoro-3,3,6-trimethyl-2,3,4,7-tetrahydroindolo[2,3-c]quinolin-1-one

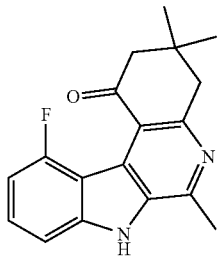

Utilizing the procedures described in Example 3 a-c except substituting 2-(4-fluoro-1H-indol-3-yl)-5,5-dimethylcyclohexane-1,3-dione for 2-(6-fluoro-1H-indol-3-yl)-5,5-dimethylcyclohexane-1,3-dione in step 3a, and 2-amino-6-fluorobenzoic acid for anthranilic acid in step 1a of Example 1, the title compound was prepared and crystallized from toluene; m.p. 246-247° C.

Example 12

Preparation of 3,6-dimethyl-2,3,4,7-tetrahydroindolo[2,3-c]quinolin-1-one

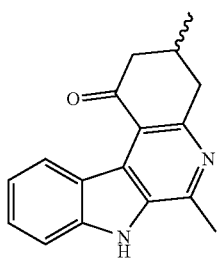

Utilizing the procedures described in Example 3 a-c except substituting 2-(1H-indol-3-yl)-5-methylcyclohexane-1,3-dione for 2-(6-fluoro-1H-indol-3-yl)-5,5-dimethylcyclohexane-1,3-dione in step 3a, and 5-methylcyclohexane-1,3-dione for 5,5-dimethylcyclohexane-1,3-dione in step 1e of Example 1, the title compound was prepared and crystallized from toluene; m.p. 218-219° C.

Example 13

Preparation of 3-isopropyl-6-methyl-2,3,4,7-tetrahydroindolo[2,3-c]quinolin-1-one

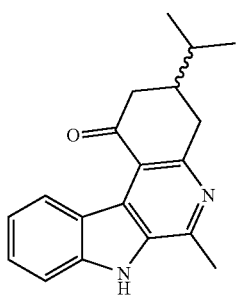

Utilizing the procedures described in Example 3 a-c except substituting 2-(1H-indol-3-yl)-5-isopropyl-cyclohexane-1,3-dione for 2-(6-fluoro-1H-indol-3-yl)-5,5-dimethylcyclohexane-1,3-dione in step 3a, and 5-isopropylcyclohexane-1,3-dione for 5,5-dimethylcyclohexane-1,3-dione in step 1e of Example 1, the title compound was prepared and crystallized from toluene; m.p. 248-249° C.

Example 14

Preparation of 6-methyl-3'H-spirocyclohexane-2,3,4,7-tetrahydroindolo[2,3-c]quinolin-1-one

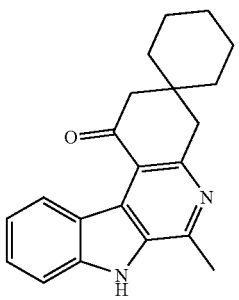

Utilizing the procedures described in Example 3 a-c except substituting 3-(1H-indol-3-yl)-spiro[5.5]undecane-2,4-dione for 2-(6-fluoro-1H-indol-3-yl)-5,5-dimethylcyclo-hexane-1,3-dione in step 3a, and spiro[5.5]undecane-2,4-dione-the for 5,5-dimethylcyclohexane-1,3-dione in step 1e of Example 1, title compound was prepared and crystallized from toluene; m.p. 245-246° C.

Example 15

Preparation of 10-chloro-3,3,6-trimethyl-2,3,4,7-tetrahydroindolo[2,3-c]quinolin-1-one

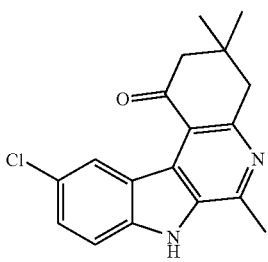

Method A. Utilizing the procedures described in Example 3 a-c except substituting 2-(5-chloro-1H-indol-3-yl)-5,5-dimethylcyclohexane-1,3-dione for 2-(6-fluoro-1H-indol-3-yl)-5,5-dimethylcyclohexane-1,3-dione in step 3a, and 2-amino-5-chlorobenzoic acid for anthranilic acid in step 1a of Example 1, the title compound was prepared and crystallized from toluene; m.p. 244-246° C.

Method B. A mixture was prepared on addition of 85% phosphorous acid (1.7 mL, 25 mmol) to acetic anhydride (21.6 mL, 200 mmol) at 5-10° C. under stirring, and then 2-(1-acetyl-5-chloro-1H-indol-3-yl)-5,5-dimethylcyclohexane-1,3-dione (2.6 g, 10 mmol), prepared by utilizing the procedures described in Example 1 a-e except substituting 2-amino-5-chlorobenzoic acid for anthranilic acid in step 1a, was added to the mixture. The reaction mixture was heated at 95-100° C. for 30 min, cooled to 60-70° C., and water (1.8 mL) was added dropwise over 15 min at 60-70° C., and then ammonium acetate (7.71 g, 100 mmol) was added. The mixture was heated at 100-120° C. for 1 h under stirring, and then acetic acid (12 mL), which was formed during the reaction, was distilled off in vacuum. The residue was cooled and aqueous ammonia (15 mL) was added. The precipitate was filtered off, washed with water, dried and purified by crystallized from toluene (110 mL) with addition of neutral aluminum oxide to give 2.5 g (80%) of pale yellow crystals. M.p. of the compound was identical to that of the product prepared by Method A.

Example 16

Preparation of 6-methyl-3-phenyl-2,3,4,7-tetrahydroindolo[2,3-c]quinolin-1-one

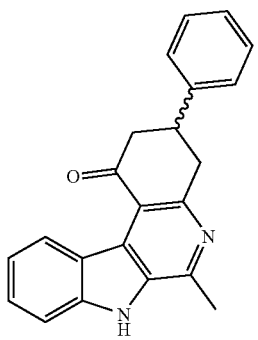

Utilizing the procedures described in Example 3 a-c except substituting 2-(1H-indol-3-yl)-5-phenyl-cyclohexane-1,3-dione for 2-(6-fluoro-1H-indol-3-yl)-5,5-dimethylcyclohexane-1,3-dione in step 3a, and 5-phenylcyclohexane-1,3-dione for 5,5-dimethylcyclohexane-1,3-dione in step 1e of Example 1, the title compound was prepared and crystallized from toluene; m.p. 246-248° C.

Example 17

Preparation of 3,6-dimethyl-2,3,4,7-tetrahydroindolo[2,3-c]quinolin-1-one oxime

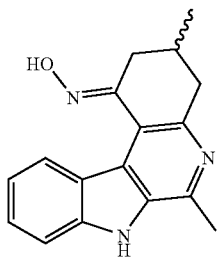

A mixture of 3,6-dimethyl-2,3,4,7-tetrahydroindolo[2,3-c]quinolin-1-one of Example 12 (0.26 g, 1 mmol), ethanol (4 mL), pyridine (0.15 mL, 1.85 mmol) and hydroxylamine hydrochloride (0.1 g, 1.5 mmol) was refluxed for 3 h. The mixture was cooled, the solid product was filtered off, washed with ethanol, dried, and dissolved in hot water (20 mL). Aqueous ammonium hydroxide was added to pH 9. The precipitate was collected, washed with water, dried and crystallized from ethanol-water, 1:1 to give 0.17 g (61%) of colorless crystals; m.p. 282-283° C.

Example 18

Preparation of 3,3,6-trimethyl-2,3,4,7-tetrahydroindolo[2,3-c]quinolin-1-one oxime

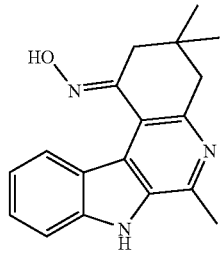

Utilizing the procedures described in Example 17 except substituting 3,3,6-trimethyl-2,3,4,7-tetrahydroindolo[2,3-c]quinolin-1-one for 3,6-dimethyl-2,3,4,7-tetrahydroindolo[2,3-c]quinolin-1-one in step 3a, the title compound was prepared and crystallized from ethanol-water, 1:1; m.p. 293-294° C.

Example 19

Preparation of 9,10-difluoro-3,3,6-trimethyl-2,3,4,7-tetrahydroindolo[2,3-c]quinolin-1-one

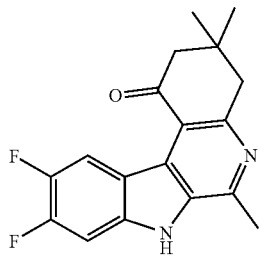

Utilizing the procedures described in Example 3 a-c except substituting 2-(5,6-difluoro-1H-indol-3-yl)-5,5-dimethylcyclohexane-1,3-dione for 2-(6-fluoro-1H-indol-3-yl)-5,5-dimethylcyclohexane-1,3-dione in step 3a, and 2-amino-4,5-difluorobenzoic acid for anthranilic acid in step 1a of Example 1, the title compound was prepared and crystallized from toluene; m.p. 260-252° C.

Example 20

Preparation of 6-ethyl-3,3-dimethyl-2,3,4,7-tetrahydro-indolo[2,3-c]quinolin-1-one

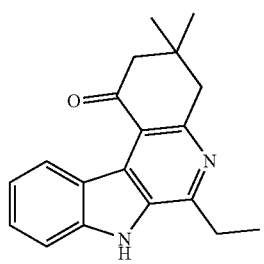

Utilizing the procedures described in Example 3 a-c except substituting 2-(1H-indol-3-yl)-5,5-dimethylcyclohexane-1, 3-dione for 2-(6-fluoro-1H-indol-3-yl)-5,5-dimethyl-cyclohexane-1,3-dione in step 3a, and propionic anhydride for acetic anhydride in step 3b, the title compound was prepared and crystallized from toluene; m.p. 188-190° C.

Example 21

Preparation of 6-isopropyl-3,3-dimethyl-2,3,4,7-tetrahydroindolo[2,3-c]quinolin-1-one

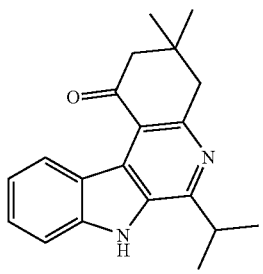

Utilizing the procedures described in Example 3 a-c except substituting 2-(1H-indol-3-yl)-5,5-dimethylcyclohexane-1,3-dione for 2-(6-fluoro-1H-indol-3-yl)-5,5-dimethyl-cyclohexane-1,3-dione in step 3a, and isobutyric anhydride for acetic anhydride in step 3b, the title compound was prepared and crystallized from toluene; m.p. 176-178° C.

Example 22

Preparation of 10-fluoro-3,3,6-trimethyl-2,3,4,7-tetrahydroindolo[2,3-c]quinolin-1-one

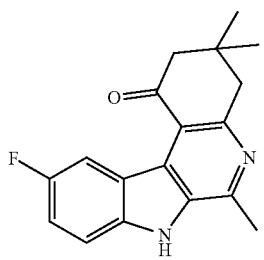

Utilizing the procedures described in Example 3 a-c except substituting 2-(5-fluoro-1H-indol-3-yl)-5,5-dimethylcyclohexane-1,3-dione for 2-(6-fluoro-1H-indol-3-yl)-5,5-dimethylcyclohexane-1,3-dione in step 3a, and 2-amino-5-fluorobenzoic acid for anthranilic acid in step 1a of Example 1, the title compound was prepared and crystallized from toluene; m.p. 229-230° C.

Example 23

Preparation of 3,3,6-trimethyl-2,3,4,7-tetrahydro-1H-indolo[2,3-c]quinoline

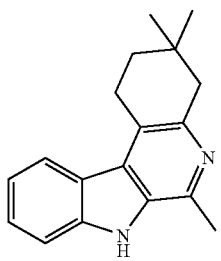

Utilizing procedures described in Example 2 except substituting 3,3,6-trimethyl-2,3,4,7-tetrahydroindolo[2,3-c]quinolin-1-one of Example 4 for 3,3-dimethyl-2,3,4,7-tetrahydroindolo-[2,3-c]quinolin-1-one, the title compound was prepared and crystallized from toluene; m.p. 241-243° C.

Example 24

Preparation of 7-N-ethyl-3,3,6-trimethyl-2,3,4,7-tetrahydroindolo[2,3-c]quinolin-1-one

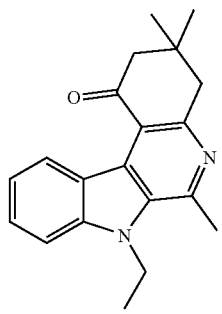

A solution of 3,3,6-trimethyl-2,3,4,7-tetrahydroindolo[2,3-c]quinolin-1-one of Example 4 (0.28 g, 1 mmol) in anhydrous N,N-dimethylformamide (4 mL) was added dropwise at room temperature under stirring to a suspension of sodium hydride (60% dispersion in mineral oil, 0.051 g, 1.3 mmol) in anhydrous N,N-dimethylformamide (4 mL). The reaction mixture was stirred for 2 h at room temperature, and then 1-iodoethane (0.19 g, 1.2 mmol) was added dropwise. The mixture was stirred at room temperature until the reaction was completed (4 h, thin layer chromatography control). The reaction mixture was diluted with water (25 mL) and brine (10 mL), and then extracted with ethyl acetate (3×15 mL). The combined organic layers were dried over anhydrous sodium sulfate, and ethyl acetate was distilled off in vacuum to give the crude product (0.18 g, 60%). Crystallization from hexanes yielded the pure product as light orange crystals; m.p. 174-177° C.

Example 25

Preparation of 7-N-propyl-3,3,6-trimethyl-2,3,4,7-tetrahydroindolo[2,3-c]quinolin-1-one

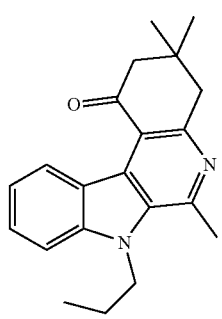

Utilizing procedures described in Example 24 except substituting 1-iodopropane for 1-iodoethane, the title compound was prepared and crystallized from hexanes; m.p. 123-125° C.

The biological activity of the compounds of Structure (I) were analyzed using standard binding assays. Examples of calcium channel and $GABA_A$ chloride channel binding assays are well known in the art [for example, see R. Gloud, et al., Molecular Pharmacology 25:235-241 (1984); F. J. Ehlert, et al., Life Sci. 30:2191-2202 (1982); H. Schoemaker, et al., Eur. J. Pharmacol. 111:273-277 (1985); L. Lawrence, et al., J. Neurochem. 45: 798-804 (1986); L. M. Cole, et al., Life Sci. 35: 1755-1762 (1984)]. The methodology described in those publications is incorporated herein by reference.

The biological activity of the compounds of Structure (I) were demonstrated by the following tests which were performed at NovaScreen, a Caliper Life Science Company (Hanover, Md., U.S.A.) by the standard techniques and procedures known in the art:

(I) Calcium Channel, Type L (Dihydropyridine Site), [$^3$H] Nitrendipine Radioligand Binding Assay $K_D$ (binding affinity): 0.20 nM. $B_{max}$ (receptor number): 166 fmol/mg tissue (wet weight). Receptor source: rat cortical membranes. Radioligand: [$^3$H]Nitrendipine (70-80 Ci/mmol). Final ligand concentration: [0.2 nM]. Non-specific determinant: Nifedipine [1.0 µM]. Reference compound: Nifedipine. Positive control: Nifedipine.

The procedure was as follows: Reactions were carried out in 50 mM TRIS.HCl (tromethamine hydrochloride) (pH 7) at 25° C. for 60 min. The reaction was terminated by rapid vacuum filtration onto glass fiber filters. Radioactivity trapped onto the filters was determined and compared to control values in order to ascertain any interactions of test compound with the Nitrendipine binding site [see R. Gould et al., Tissue Heterogenecity of Calcium Channel Antagonist Binding Sites Labeled by [$^3$H]Nitrendipine. Molecular Pharmacology, 25: 235-241 (1984); F. J. Ehlert et al., The Binding of [$^3$H]Nitrendipine to Receptors for Calcium Channel Antagonists in the Heart, Cerebral Cortex, and Ileum of Rats. Life Sci. 30: 2191-2202 (1982)].

(II) Calcium Channel, Type L (Benzothiazepine Site), [$^3$H] Diltiazem Radioligand Binding Assay $K_D$ (binding affinity): 34 nM. $B_{max}$ (receptor number): 24.2 fmol/mg tissue (wet weight). Receptor source: rat cortical membranes. Radioligand: [$^3$H]Diltiazem, cis(+) (70-87 Ci/mmol). Final ligand concentration: [5.0 nM]. Non-specific determinant: Diltiazem hydrochloride [10 µM]. Reference compound: Diltiazem hydrochloride. Positive control: Diltiazem hydrochloride.

The procedure was as follows: Reactions were carried out in 50 mM TRIS-HCl (pH 7) containing 0.1% BSA at 25° C. for 90 min. The reaction was terminated by rapid vacuum filtration onto glass fiber filters. Radioactivity trapped onto the filters was determined and compared to control values in order to ascertain any interactions of test compound with the Diltiazem binding site [see H. Schoemaker and S. Z. Langer. [$^3$H]Diltiazem Binding to Calcium Channel Antagonists Recognition Sites in Rat Cerebral Cortex. Eur. J. Pharmacol. 111: 273-277 (1985)].

(III) GABA$_A$, Chloride Channel (tert-Butylbicycloorthobenzoate (TBOB) Site), [$^3$H]TBOB Radioligand Binding Assay $K_D$ (binding affinity): 45 nM. $B_{max}$ (receptor number): 116.7 fmol/mg tissue (wet weight). Receptor source: rat cortical membranes. Radioligand: [$^3$H]TBOB (20-60 Ci/mmol). Final ligand concentration: [20 nM]. Non-specific determinant: tert-butylbicyclophosphorothionate (TBPS) [10 µM]. Reference compound: tert-butylbicyclophosphorothionate (TBPS). Positive control: tert-butylbicyclophosphorothionate (TBPS).

The procedure was as follows: Reactions were carried out in 20 mM NaKPO$_4$/500 mM NaCl (pH 7.5) at 25° C. for 75 min. The reaction was terminated by rapid vacuum filtration onto glass fiber filters. Radioactivity trapped onto the filters was determined and compared to control values in order to ascertain any interactions of test compound with the TBOB binding site [see L. Lawrence, et al. T[$^3$H]butylbicycloorthobenzoate: A New Radioligand Probe for Gamma-Aminobutyric Acid-regulated Chloride Ionophore. J. Neurochem. 45: 798-804 (1986); L. M. Cole, et al. Similar Properties of [$^{35}$S]t-butylbicyclophosphothionate Receptor and Coupled Components of the GABA Receptor-Ionophore Complex in Brains of Human, Cow, Rat, Chicken, and Fish. Life Sci. 35: 1755-1762 (1984)].

All compounds were tested at 5 concentrations in duplicate with the highest concentration being 50 µM.

In general, those compounds having lower IC$_{50}$ values in the [$^3$H]Nitrendipine and [$^3$H]Diltiazem binding assays and higher IC$_{50}$ values in the [$^3$H]TBOB binding assay are more preferred compounds. Compounds useful in the current invention have IC$_{50}$ values in the [$^3$H]Nitrendipine and [$^3$H]Diltiazem binding assays below 50 µM. Preferred compounds are those having an IC$_{50}$ of 10 µM or lower in the [$^3$H]Nitrendipine and [$^3$H]Diltiazem binding assays, and an IC$_{50}$ of 3 µM or higher in the [$^3$H]TBOB binding assay. More preferred compounds are those having an IC$_{50}$ of 6 µM or lower in the [$^3$H]Nitrendipine and [$^3$H]Diltiazem binding assays, and an IC$_{50}$ of 3 µM or higher in the [$^3$H]TBOB binding assay. Even more preferred compounds are those having an IC$_{50}$ 3 µM or lower in the [$^3$H]Nitrendipine and [$^3$H]Diltiazem binding assays, and an IC$_{50}$ of 3 µM or higher in the [$^3$H]TBOB binding assay. Most preferred compounds are those having an IC$_{50}$ of 1 µM or lower in the [$^3$H]Nitrendipine and [$^3$H]Diltiazem binding assays, and an IC$_{50}$ of 3 µM or higher in the [3H]TBOB binding assay.

All publications, including but not limited to patents and patent applications, cited in this specification are herein incorporated by reference as if each individual publication were specifically and individually indicated to be incorporated by reference herein and as though fully set forth.

The above description fully discloses the invention including preferred embodiments thereof. Modifications and improvements of the embodiments specifically disclosed herein are within the scope of the following claims. Without further elaboration, it is believed that one skilled in the area can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

It will be obvious to those having skill in the art that many changes may be made to the details of the above-described embodiments without departing from the underlying principles of the invention. The scope of the present invention should, therefore, be determined only by the following claims.

The invention claimed is:

1. A compound having the chemical formula:

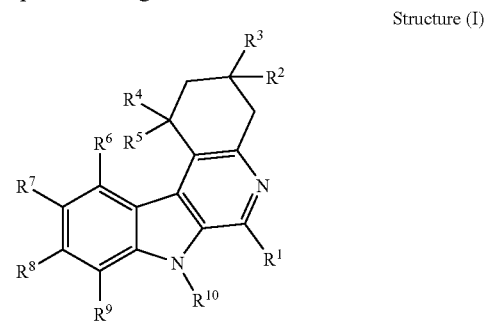

Structure (I)

wherein:

R$^1$ is one of: H, lower alk, cycloalk, aryl, arylalkyl;

R$^2$ and R$^3$ are each independently selected from one of: H, lower alk, cycloalk, aryl, arylalkyl; or R$^2$ and R$^3$ are together —(CH$_2$)$_n$— and n is 6, 5 or 4; or R$^2$ and R$^3$ are together —CH(lower alkyl)(CH$_2$)$_n$— and n is 5, 4 or 3;

R$^4$ and R$^5$ are each independently selected from one of: H, NH$_2$, OH or lower alk; or R$^4$ and R$^5$ are together O, S or NOH;

R$^6$ is independently selected from the group consisting of: hydrogen or F,

R$^7$ and R$^8$ are independently selected from the group consisting of:
hydrogen, F, Cl, or methoxy, wherein at least one of R$^6$, R$^7$, and R$^8$ is not hydrogen;

R$^9$ is H;

R$^{10}$ is one of: H, lower alkyl, cycloalk, aryl, arylalkyl; or pharmaceutically acceptable tautomers thereof.

2. The compound according to claim 1, wherein at least one of R$^6$, R$^7$, or R$^8$ is fluorine.

3. The compound according to claim 1, wherein at least one of R$^7$ or R$^8$ is methoxy.

4. The compound according to claim 1, wherein at least one of R$^7$ or R$^8$ is chlorine.

5. A pharmaceutical composition comprising a compound represented by Structure (I) according to claim 1, and a pharmaceutically acceptable diluent or excipient.

6. A method for preparing substituted 2,3,4,7-tetrahydroindolo[2,3-c]quinolin-1-ones according to claim 1, comprising reacting substituted 1-oxo-2,3,4,7-tetrahydro-1H-5-oxonia-7-azabenzo[c]fluorene perchlorates, dihydrophosphates or tetrafluoroborates with ammonium hydroxide or ammonium acetate.

7. A method for preparing substituted 2,3,4,7-tetrahydroindolo[2,3-c]quinolines, comprising reacting substituted 2,3,4,7-tetrahydroindolo[2,3-c]quinolin-1-ones according to claim 1 with hydrazine hydrate.

8. A method of ameliorating a subject's condition, having a central nervous system disease or disorder that is mediated by calcium channels, comprising the administration to a subject in need of treatment thereof an effective amount of a compound represented by Structure (I) according to claim 1, and wherein the subject's condition results from at least one of neuronal loss following global and focal ischemia, or ischemia-reperfusion injury.

9. A method of ameliorating a subject's condition, having a central nervous system disease or disorder that is mediated by calcium channels, comprising the administration to a subject in need of treatment thereof an effective amount of a compound represented by Structure (I) according to claim 1, and wherein said central nervous system disease or disorder causes convulsion.

10. A method of ameliorating a subject's condition, having a central nervous system disease or disorder that is mediated by calcium channels, comprising the administration to a subject in need of treatment thereof an effective amount of a compound represented by Structure (I) according to claim 1, and wherein said central nervous system disease or disorder causes at least one of chronic pain or neuropathic pain.

11. A method of ameliorating a subject's condition, having a central nervous system disease or disorder that is mediated by calcium channels, comprising the administration to a subject in need of treatment thereof an effective amount of a compound represented by Structure (I) according to claim 1, and wherein said central nervous system disease or disorder is depression.

12. A method of ameliorating a subject's condition, having a central nervous system disease or disorder that is mediated by calcium channels, comprising the administration to a subject in need of treatment thereof an effective amount of a compound represented by Structure (I) according to claim 1, and wherein said central nervous system disease or disorder is a neurodegenerative condition.

13. A compound selected from at least one of:
9-fluoro-3,3,6-trimethyl-2,3,4,7-tetrahydroindolo[2,3-c]quinolin-1-one;
9-fluoro-3,3-dimethyl-2,3,4,7-tetrahydroindolo[2,3-c]quinolin-1-one;
10-methoxy-3,3-dimethyl-2,3,4,7-tetrahydroindolo[2,3-c]quinolin-1-one;
10-methoxy-3,3,6-trimethyl-2,3,4,7-tetrahydroindolo[2,3-c]quinolin-1-one;
9-chloro-3,3-dimethyl-2,3,4,7-tetrahydroindolo[2,3-c]quinolin-1-one;
9-chloro-3,3,6-trimethyl-2,3,4,7-tetrahydroindolo[2,3-c]quinolin-1-one;
9-methoxy-3,3,6-trimethyl-2,3,4,7-tetrahydroindolo[2,3-c]quinolin-1-one;
11-fluoro-3,3,6-trimethyl-2,3,4,7-tetrahydroindolo[2,3-c]quinolin-1-one;
10-chloro-3,3,6-trimethyl-2,3,4,7-tetrahydroindolo[2,3-c]quinolin-1-one;
9,10-difluoro-3,3,6-trimethyl-2,3,4,7-tetrahydroindolo[2,3-c]quinolin-1-one; and
10-fluoro-3,3,6-trimethyl-2,3,4,7-tetrahydroindolo[2,3-c]quinolin-1-one.

14. A method of ameliorating a subject's condition, having a central nervous system disease or disorder that is mediated by calcium channels, comprising administering to a subject in need thereof an effective amount of a compound according to Structure (I):

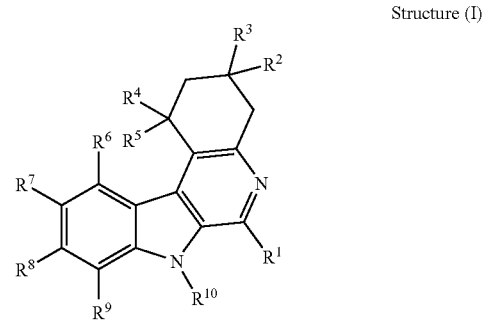

Structure (I)

wherein:

R$^1$ is one of: H, lower alk, cycloalk, aryl, arylalkyl;

R$^2$ and R$^3$ are each independently selected from one of: H, lower alkyl, cycloalk, aryl, arylalkyl; or R$^2$ and R$^3$ are together —(CH$_2$)$_n$— and n is 6, 5 or 4; or R$^2$ and R$^3$ are together —CH(lower alkyl)(CH$_2$)$_n$— and n is 5, 4 or 3;

R$^4$ and R$^5$ are each independently selected from one of: H, NH$_2$, OH or lower alk;

or R$^4$ and R$^5$ are together O, S or NOH;

R$^6$, R$^7$, R$^8$, and R$^9$ are each independently selected from the group consisting of:
H, halogen, CN, CF$_3$, OCF$_3$, lower alkyl, cycloalk, lower alkoxy, NH-lower alk, NH-alkylaryl, N(lower alkyl)$_2$, C(O)OH, C(O)-lower alk, OH, OC(O)-lower alkyl; and R$^{10}$ is one of: H, lower alkyl, cycloalk, aryl, arylalkyl, and wherein said central nervous system disease or disorder causes convulsion.

15. The method according to claim 14, wherein:

R$^1$ is methyl;

R$^2$ and R$^3$ are each methyl;

R$^4$ and R$^5$ are together O;

R$^6$, R$^7$, R$^8$, and R$^9$ are each H; and

R$^{10}$ is H.

16. The method according to claim 14, wherein the compound is 3,3,6-trimethyl-2,3,4,7-tetrahydroindolo[2,3-c]quinolin-1-one.

17. A method of ameliorating a subject's condition, having a central nervous system disease or disorder that is mediated by calcium channels, comprising administering to a subject in need thereof an effective amount of a compound according to Structure (I):

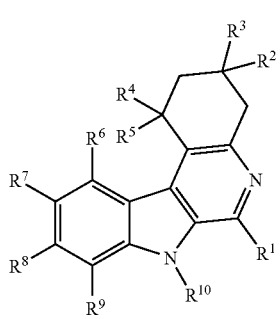

Structure (I)

wherein:
$R^1$ is one of: H, lower alk, cycloalk, aryl, arylalkyl;
$R^2$ and $R^3$ are each independently selected from one of: H, lower alkyl, cycloalk, aryl, arylalkyl; or $R^2$ and $R^3$ are together —$(CH_2)_n$— and n is 6, 5 or 4; or
$R^2$ and $R^3$ are together —CH(lower alkyl)$(CH_2)_n$— and n is 5, 4 or 3;
$R^4$ and $R^5$ are each independently selected from one of: H, $NH_2$, OH or lower alk;
or $R^4$ and $R^5$ are together O, S or NOH;
$R^6$, $R^7$, $R^8$, and $R^9$ are each independently selected from the group consisting of:
H, halogen, CN, $CF_3$, $OCF_3$, lower alkyl, cycloalk, lower alkoxy, NH-lower alk, NH-alkylaryl, N(lower alkyl)$_2$, C(O)OH, C(O)-lower alk, OH, OC(O)-lower alkyl; and
$R^{10}$ is one of: H, lower alkyl, cycloalk, aryl, arylalkyl,
and wherein said central nervous system disease or disorder causes at least one of chronic pain or neuropathic pain.

18. The method according to claim 17, wherein:
$R^1$ is methyl;
$R^2$ and $R^3$ are each methyl;
$R^4$ and $R^5$ are together O;
$R^6$, $R^7$, $R^8$, and $R^9$ are each H; and
$R^{10}$ is H.

19. The method according to claim 17, wherein the compound is 3,3,6-trimethyl-2,3,4,7-tetrahydroindolo[2,3-c]quinolin-1-one.

20. A method of ameliorating a subject's condition, having a central nervous system disease or disorder that is mediated by calcium channels, comprising administering to a subject in need thereof an effective amount of a compound according to Structure (I):

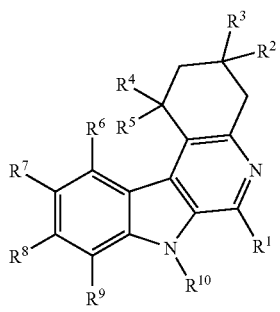

Structure (I)

wherein:
$R^1$ is one of: H, lower alk, cycloalk, aryl, arylalkyl;
$R^2$ and $R^3$ are each independently selected from one of: H, lower alkyl, cycloalk, aryl, arylalkyl; or $R^2$ and $R^3$ are together —$(CH_2)_n$— and n is 6, 5 or 4; or
$R^2$ and $R^3$ are together —CH(lower alkyl)$(CH_2)_n$— and n is 5, 4 or 3;
$R^4$ and $R^5$ are each independently selected from one of: H, $NH_2$, OH or lower alk;
or $R^4$ and $R^5$ are together O, S or NOH;
$R^6$, $R^7$, $R^8$, and $R^9$ are each independently selected from the group consisting of:
H, halogen, CN, $CF_3$, $OCF_3$, lower alkyl, cycloalk, lower alkoxy, NH-lower alk, NH-alkylaryl, N(lower alkyl)$_2$, C(O)OH, C(O)O-lower alk, OH, OC(O)-lower alkyl; and
$R^{10}$ is one of: H, lower alkyl, cycloalk, aryl, arylalkyl,
and wherein said central nervous system disease or disorder is depression.

21. The method according to claim 20, wherein:
$R^1$ is methyl;
$R^2$ and $R^3$ are each methyl;
$R^4$ and $R^5$ are together O;
$R^6$, $R^7$, $R^8$, and $R^9$ are each H; and
$R^{10}$ is H.

22. The method according to claim 20, wherein the compound is 3,3,6-trimethy-2,3,4,7-tetrahydroindolo[2,3-c]quinolin-1-one.

23. A method of ameliorating a subject's condition, having a central nervous system disease or disorder that is mediated by calcium channels, comprising administering to a subject in need thereof an effective amount of a compound according to Structure (I):

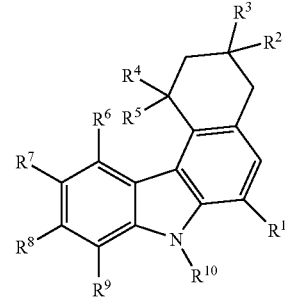

Structure (I)

wherein:
$R^1$ is one of: H, lower alk, cycloalk, aryl, arylalkyl;
$R^2$ and $R^3$ are each independently selected from one of: H, lower alkyl, cycloalk, aryl, arylalkyl; or $R^2$ and $R^3$ are together —$(CH_2)_n$— and n is 6, 5 or 4; or
$R^2$ and $R^3$ are together —CH(lower alkyl)$(CH_2)_n$— and n is 5, 4 or 3;
$R^4$ and $R^5$ are each independently selected from one of: H, $NH_2$, OH or lower alk;
or $R^4$ and $R^5$ are together O, S or NOH;
$R^6$, $R^7$, $R^8$, and $R^9$ are each independently selected from the group consisting of:
H, halogen, CN, $CF_3$, $OCF_3$, lower alkyl, cycloalk, lower alkoxy, NH-lower alk, NH-alkylaryl, N(lower alkyl)$_2$, C(O)OH, C(O)O-lower alk, OH, OC(O)-lower alkyl; and
$R^{10}$ is one of: H, lower alkyl, cycloalk, aryl, arylalkyl,
and wherein said central nervous system disease or disorder is at least one of Parkinson's disease, Huntington's disease, or amyotrophic lateral sclerosis.

24. The method according to claim 23, wherein:
R$^1$ is methyl;
R$^2$ and R$^3$ are each methyl;
R$^4$ and R$^5$ are together O;
R$^6$, R$^7$, R$^8$, and R$^9$ are each H; and
R$^{10}$ is H.

25. The method according to claim 23, wherein the compound is 3,3,6-trimethyl-2,3,4,7-tetrahydroindolo[2,3-c]quinolin-1-one.

* * * * *